(12) United States Patent
Sasaki et al.

(10) Patent No.: US 7,448,381 B2
(45) Date of Patent: Nov. 11, 2008

(54) RESPIRATION CONTROL APPARATUS

(75) Inventors: Takeshi Sasaki, Isesaki (JP); Hidenori Tashiro, Shinagawa (JP); Yosuke Tamuro, Toda (JP)

(73) Assignee: Anzai Medical Kabushiki Kaisha, Tokyo (JP)

( * ) Notice: Subject to any disclaimer, the term of this patent is extended or adjusted under 35 U.S.C. 154(b) by 1058 days.

(21) Appl. No.: 10/659,301

(22) Filed: Sep. 11, 2003

(65) Prior Publication Data

US 2004/0082853 A1      Apr. 29, 2004

(30) Foreign Application Priority Data

Sep. 17, 2002   (JP)   ............... 2002-270054

(51) Int. Cl.
*A61M 16/00*   (2006.01)
(52) U.S. Cl. ............... 128/204.18; 128/204.23; 128/205.24
(58) Field of Classification Search ............ 128/204.18, 128/204.21, 204.23, 205.11, 205.24; 600/407–428
See application file for complete search history.

(56) References Cited

U.S. PATENT DOCUMENTS

| | | | |
|---|---|---|---|
| 3,741,208 A | | 6/1973 | Jonsson et al. |
| 4,206,754 A | * | 6/1980 | Cox et al. ............... 128/204.21 |
| 4,448,192 A | | 5/1984 | Stawitchke et al. |
| 4,883,051 A | * | 11/1989 | Westenskow et al. .. 128/204.21 |
| 5,067,494 A | | 11/1991 | Rienmueller et al. |
| 6,003,513 A | * | 12/1999 | Readey et al. ........... 128/205.24 |
| 6,041,777 A | * | 3/2000 | Faithfull et al. ......... 128/200.24 |
| 6,597,939 B1 | * | 7/2003 | Lampotang et al. ......... 600/427 |
| 6,631,716 B1 | * | 10/2003 | Robinson et al. ........ 128/204.21 |
| 7,257,436 B2 | * | 8/2007 | Sasaki et al. ................. 600/428 |
| 2003/0150455 A1 | * | 8/2003 | Bliss et al. ............. 128/204.18 |

FOREIGN PATENT DOCUMENTS

| | | |
|---|---|---|
| EP | 1 177 808 | 2/2002 |
| JP | 2-94511 | 7/1990 |
| JP | 2000-262513 | 9/2000 |
| JP | 2002-503507 | 2/2002 |
| WO | WO 99/42034 | 8/1999 |

OTHER PUBLICATIONS

NOTE: English language abstract of the above Japanese citation is provided to serve as partial translation thereof.

* cited by examiner

*Primary Examiner*—Steven O Douglas
(74) *Attorney, Agent, or Firm*—Paul A. Guss

(57) ABSTRACT

A respiration control apparatus connected to a controlled body includes a respiration circuit having an inhalation circuit and an exhalation circuit. The inhalation circuit includes a first solenoid-operated valve and a first check valve. The exhalation circuit includes a vent valve, a dehumidifying chamber, a pressure detector, a second check valve, and a second solenoid-operated valve. A central processor closes the first solenoid-operated valve and the second solenoid-operated valve based on a respiration control signal supplied from a synchronizing signal output control device, disconnecting the respiratory system of the controlled body from the outside of the respiration control apparatus.

11 Claims, 7 Drawing Sheets

RESPIRATION CONTROL APPARATUS

BACKGROUND OF THE INVENTION

1. Field of the Invention

The present invention relates to a respiration control apparatus for controlling the respiration of a respiratory moving object in a controlled body such as a human body during examination or treatment.

2. Description of the Related Art

In recent years, computer-assisted diagnosis apparatus such as CT (Computed Tomography) apparatus, CR (Computed Radiography) apparatus, MRI (Magnetic Resonance Imaging) apparatus, and radiation treatment apparatus for treating patients by applying radiation to local body regions have widely been used in the medical field.

A respiratory moving object such as an organ in a human body to be diagnosed by a computer-assisted diagnosis apparatus or treated by a radiation treatment apparatus, changes its position or volume greatly as the human body breathes. Therefore, when the computer-assisted diagnosis apparatus images the respiratory moving object, the produced image tends to be low in quality, or when the respiratory moving object is treated by the radiation treatment apparatus, the irradiation range of radiation is liable to change.

In view of the above drawbacks, various apparatus for detecting a moving state of a respiratory moving object, predicting a position of the respiratory moving object based on the detected moving state, and applying radiation at a given time based on the predicted position have been proposed. For example, Japanese laid-open patent publication No. 2000-262513 discloses an X-ray computed tomographic imaging apparatus having a respiration sensor to be attached to a human body to be imaged. The disclosed X-ray computed tomographic imaging apparatus applies X-rays to an organ in the examinee during an inhaling period in which the volume of the organ is stable, based on an output signal from the respiration sensor, and collects image data from the organ based on the applied X-rays.

However, the conventional X-ray computed tomographic imaging apparatus may not be able to collect optimum image data from a human body because the respiratory state of a human body widely differs depending on the age and the physical or mental condition of the human body. Also, the output signal from the respiration sensor widely differs depending on how the respiration sensor is attached to the human body.

SUMMARY OF THE INVENTION

It is therefore a general object of the present invention to provide a respiration control apparatus, which is capable of appropriately controlling the movement of a respiratory moving object such as an organ in a controlled body.

A major object of the present invention is to provide a respiration control apparatus which is capable of appropriately controlling the respiration of a controlled body to increase the accuracy of an image captured by an X-ray computed tomographic imaging apparatus or the accuracy with which a radiation is applied to a local region of the controlled body by a radiation treatment apparatus.

Another object of the present invention is to provide a respiration control apparatus which is capable of separately controlling the inhalation and exhalation of a controlled body.

Still another object of the present invention is to provide a respiration control apparatus which is capable of reliably connecting the respiratory system of a controlled body to the outside of the respiration control apparatus depending on the state of the controlled body.

Yet another object of the present invention is to provide a respiration control apparatus which is capable of recognizing the progress of a respiration control cycle of a controlled body.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENT

Figure 1:
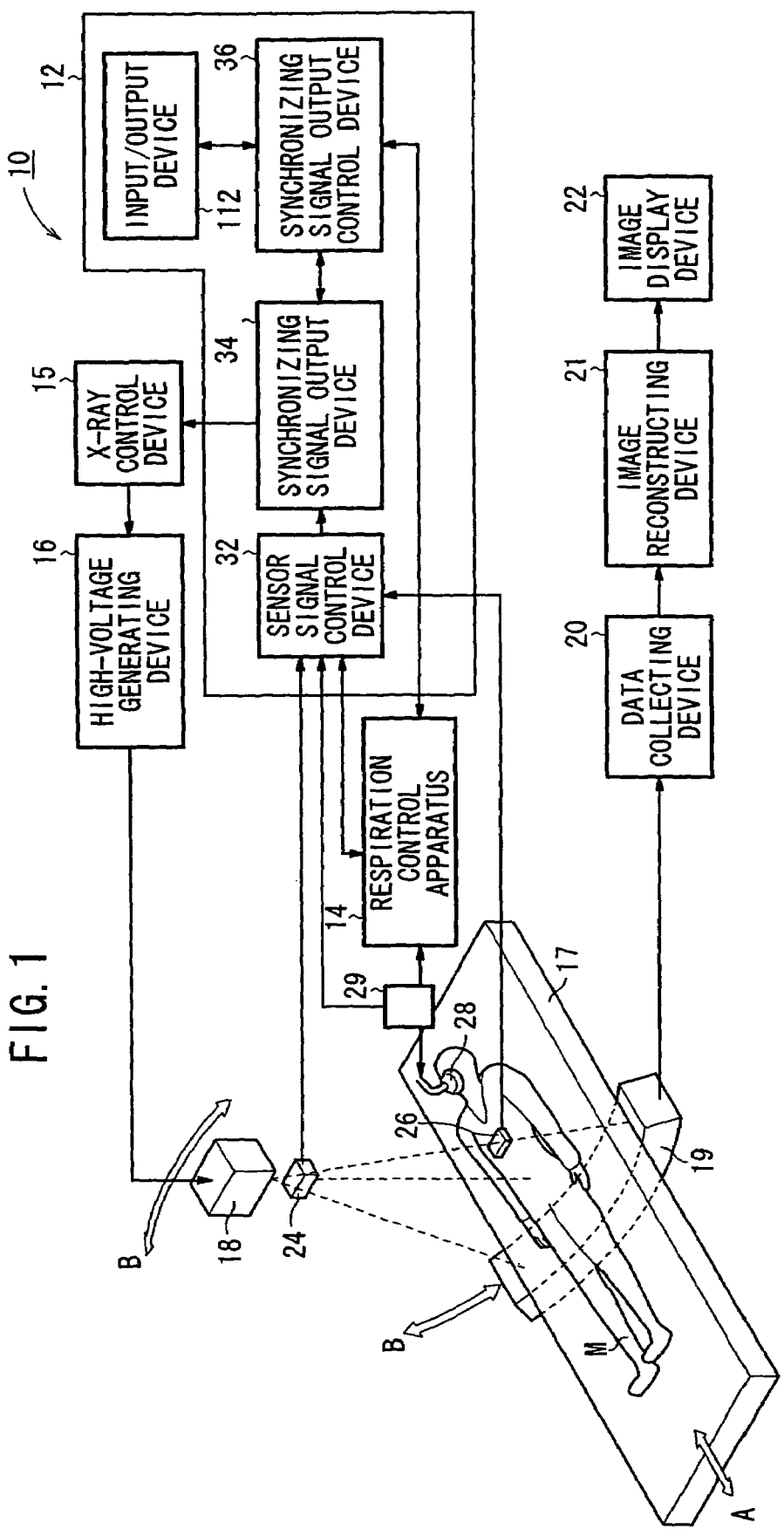
FIG. 1 is a schematic perspective view, partly in block form, of a radiation image capturing system to which a respiration control apparatus according to an embodiment of the present invention is applied.

FIG. 1 shows, partly in block form, a radiation image capturing system 10 to which a respiration control apparatus according to an embodiment of the present invention is applied.

As shown in FIG. 1, the radiation image capturing system 10 has a respiration control apparatus 14 for controlling the respiratory state of a controlled body M according to the embodiment of the present invention, a synchronizing signal generating apparatus 12 for generating a synchronizing signal based on a respiratory signal from the controlled body M, an X-ray control device 15, a high-voltage generating device 16 for generating a high voltage according to a shot signal supplied from the X-ray control device 15, a bed 17 displaceable in the direction indicated by the arrow A with the controlled body M placed thereon, an X-ray source 18 for applying X-rays to the controlled body M according to a high voltage supplied from the high-voltage generating device 16, an X-ray detector 19 for detecting X-rays that have passed through the controlled body M, a data collecting device 20 for collecting transmitted data based on X-rays detected by the X-ray detector 19, an image reconstructing device 21 for reconstructing a tomographic image of the controlled body M from transmitted data collected by the data collecting device 20, and an image display device 22 for displaying a reconstructed tomographic image on a CRT (Cathode Ray tube) or the like. The X-ray source 18 and the X-ray detector 19 are rotatable in the directions indicated by the arrow B. The components described above make up a CT (Computed Tomography) apparatus.

The synchronizing signal generating apparatus 12 comprises a sensor signal control device 32 for producing a respiration signal indicative of a respiratory state of the controlled body M, a synchronizing signal output device 34 for outputting a synchronizing signal generated based on a respiration signal to the X-ray control device 15, and a synchronizing signal output control device 36 for controlling the timing to output a synchronizing signal.

To the sensor signal control device 32, there are connected a laser sensor 24 fixedly disposed above the controlled body M for detecting a respiratory state of the controlled body M as a distance signal, a load cell 26 disposed near the diaphragm or the abdominal region of the controlled body M for detecting a respiratory state of the controlled body M as a pressure signal, and a flow rate sensor 29 coupled to a mask 28 attached to the mouth of the controlled body M for detecting a respiratory state of the controlled body M as an air flow rate signal.

Figure 2:
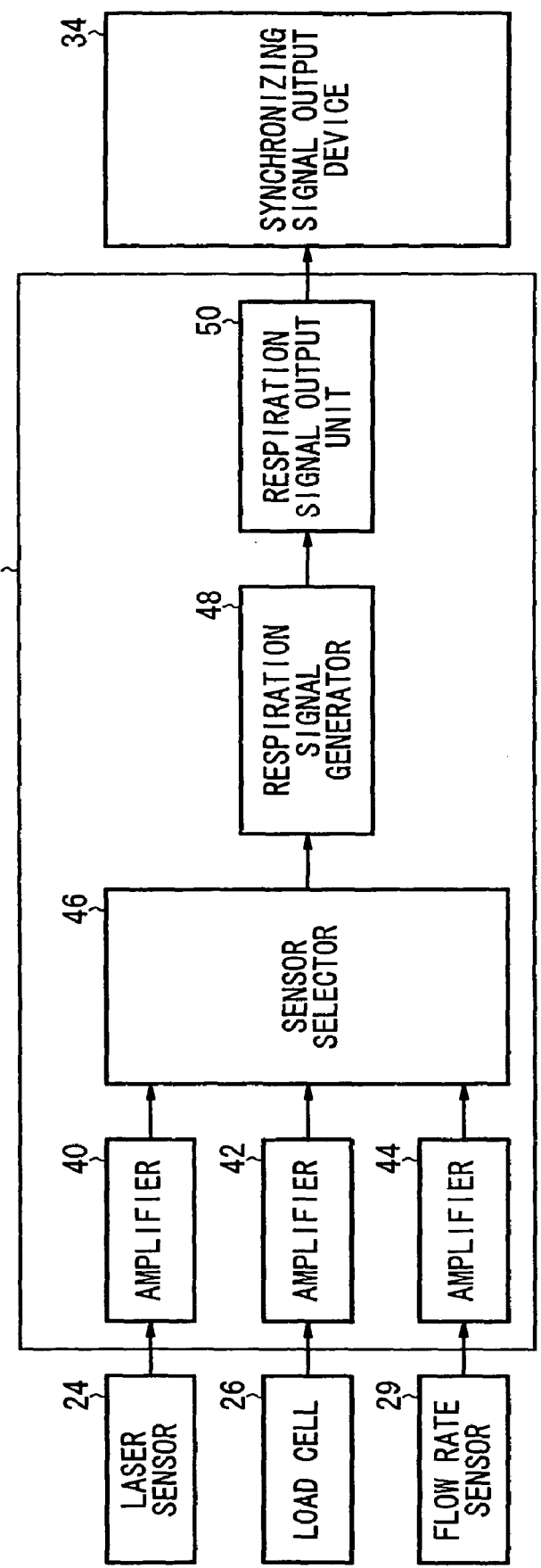
FIG. 2 is a block diagram of a sensor signal control device of a synchronizing signal generating apparatus in the radiation image capturing system.

FIG. 2 shows details of the sensor signal control device 32. As shown in FIG. 2, the sensor signal control device 32 has amplifiers 40, 42, 44 for amplifying a distance signal supplied from the laser sensor 24, a pressure signal supplied from the load cell 26, and an air flow rate signal supplied from the air flow sensor 29, respectively. The sensor signal control device 32 also has a sensor selector 46 for automatically selecting sensors according to a preset priority order, a respiration signal generator 48 for converting a signal supplied from a sensor selected by the sensor selector 46 into a predetermined level, adjusting the amplitude and offset of the converted signal, and standardizing the signal so as to be independent of the type of the sensor, the individual differences of the controlled body M, and imaging conditions, thus generating a respiration signal, and a respiration signal output unit 50 for outputting a generated respiration signal to the synchronizing signal output device 34.

Figure 3:
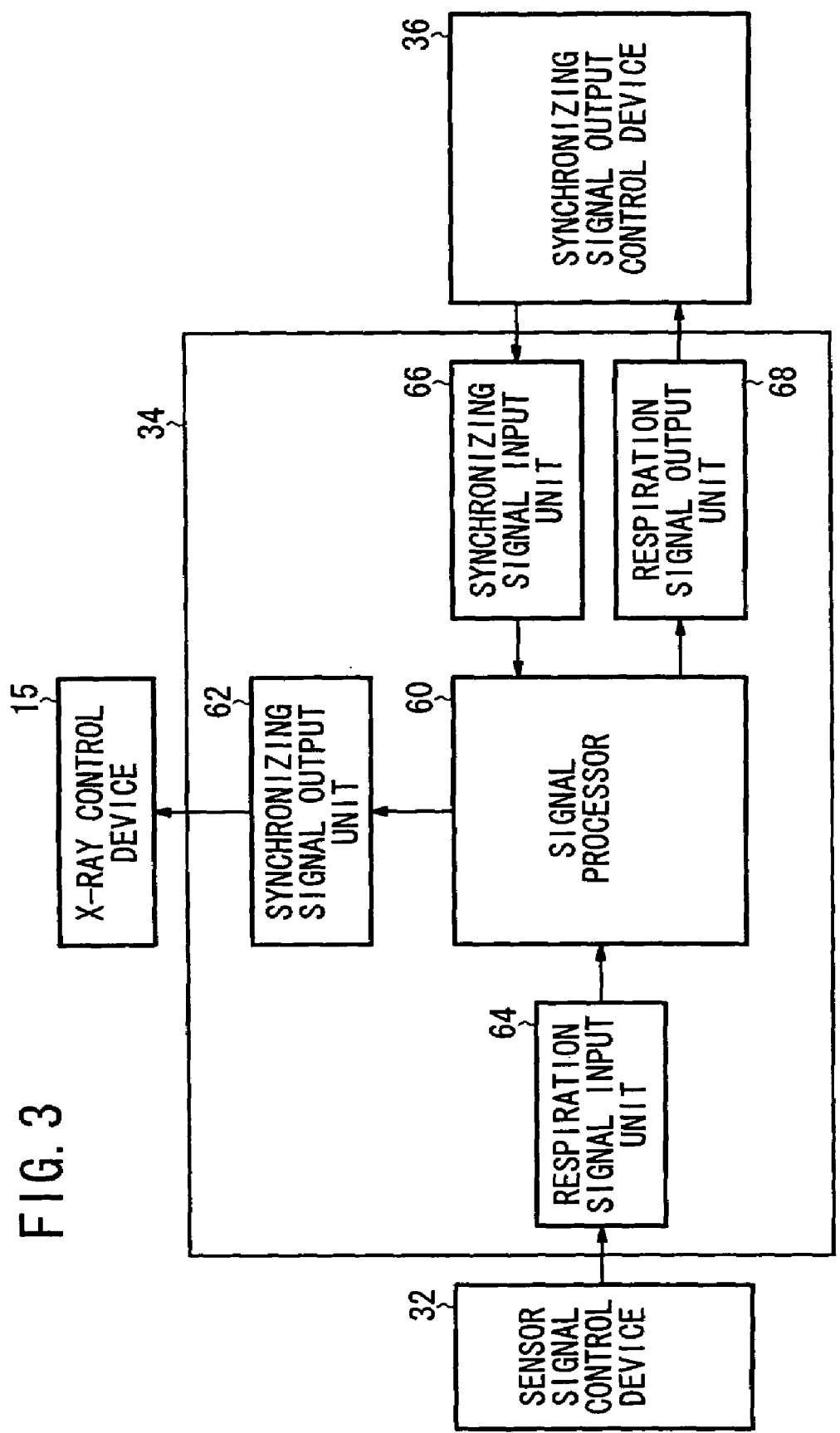
FIG. 3 is a block diagram of a synchronizing signal output device of the synchronizing signal generating apparatus.

FIG. 3 shows details of the synchronizing signal output device 34. As shown in FIG. 3, the synchronizing signal output device 34 has a signal processor 60 to which there are connected a synchronizing signal output unit 62 for outputting a synchronizing signal to the X-ray control device 15, a respiration signal input unit 64 for being supplied with a respiration signal from the sensor signal control device 32, a synchronizing signal input unit 66 for being supplied with a synchronizing signal from the synchronizing signal output control device 36, and a respiration signal output unit 68 for outputting a respiration signal to the synchronizing signal output control device 36.

The signal processor 60 outputs a synchronizing signal supplied from the synchronizing signal output control device 36 to the X-ray control device 15 through the synchronizing signal output unit 62. The signal processor 60 also calculates respiration phase data indicative of whether a respiration signal supplied from the sensor signal control device 32 represents an inhalation or an exhalation, and a maximum value of the respiration signal, and then supplies the respiration phase data and the maximum value of the respiration signal with the respiration signal, to the synchronizing signal output control device 36.

Figure 4:
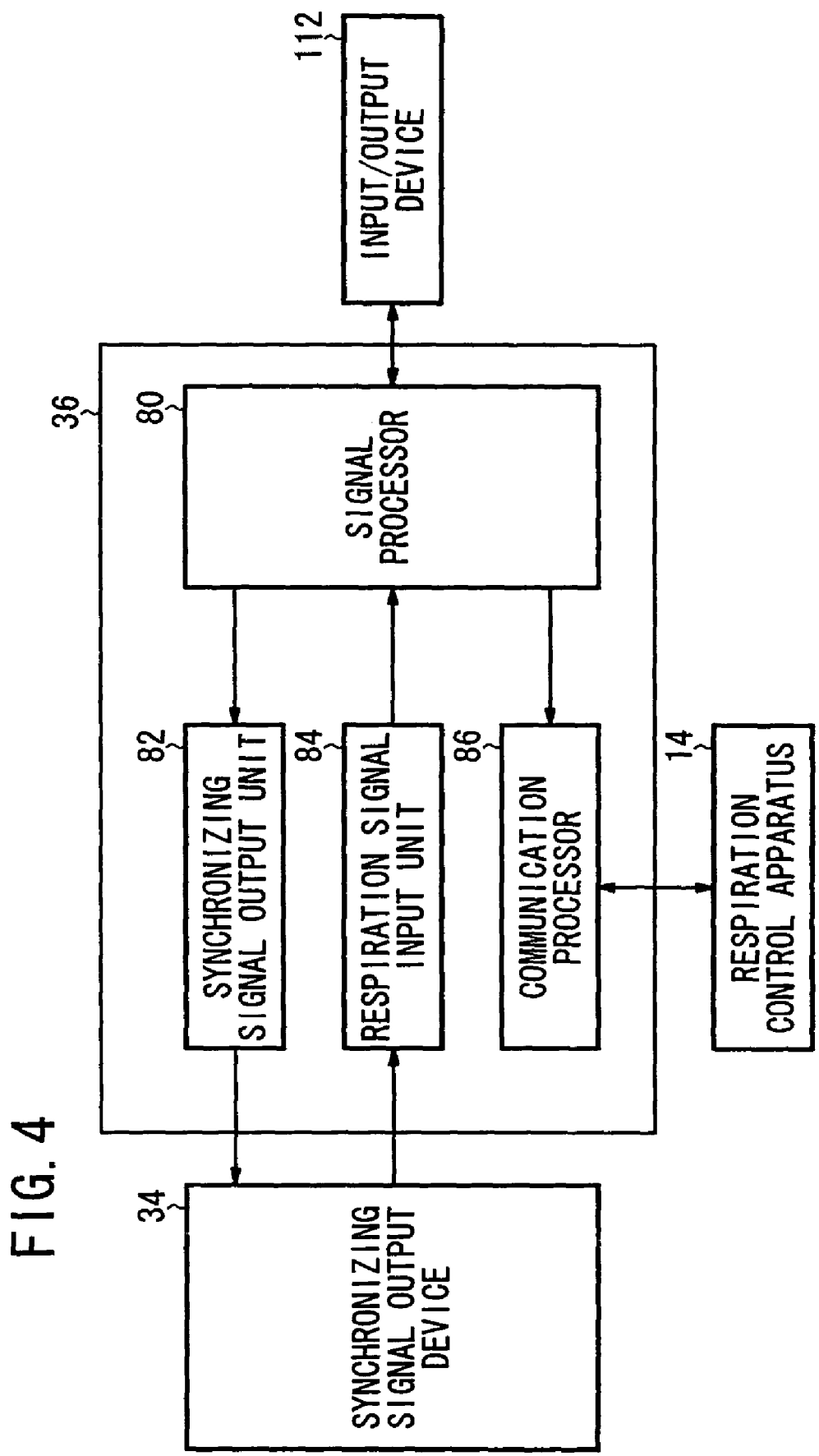
FIG. 4 is a block diagram of a synchronizing signal output control device of the synchronizing signal generating apparatus.

FIG. 4 shows details of the synchronizing signal output control device 36. As shown in FIG. 4, the synchronizing signal output control device 36 has a signal processor 80 to which there are connected a synchronizing signal output unit 82 for outputting a synchronizing signal to the synchronizing signal output device 34, a respiration signal input unit 84 for being supplied with a respiration signal from the synchronizing signal output device 34, and a communication processor 86 for communicating with the respiration control apparatus 14. An input/output device 112 having a CRT, a mouse, a keyboard, etc. is connected to the signal processor 80.

The signal processor 80 generates a respiration control signal and a synchronizing signal from a respiration signal obtained from the synchronizing signal output device 34 through the respiration signal input unit 84 and respiration control conditions established by the input/output device 112. The signal processor 80 also outputs the generated respiration control signal to the respiration control apparatus 14, and outputs the synchronizing signal to the X-ray control device 15 through the synchronizing signal output device 34. The respiration control conditions and the respiration control signal will be described later on.

Figure 5:
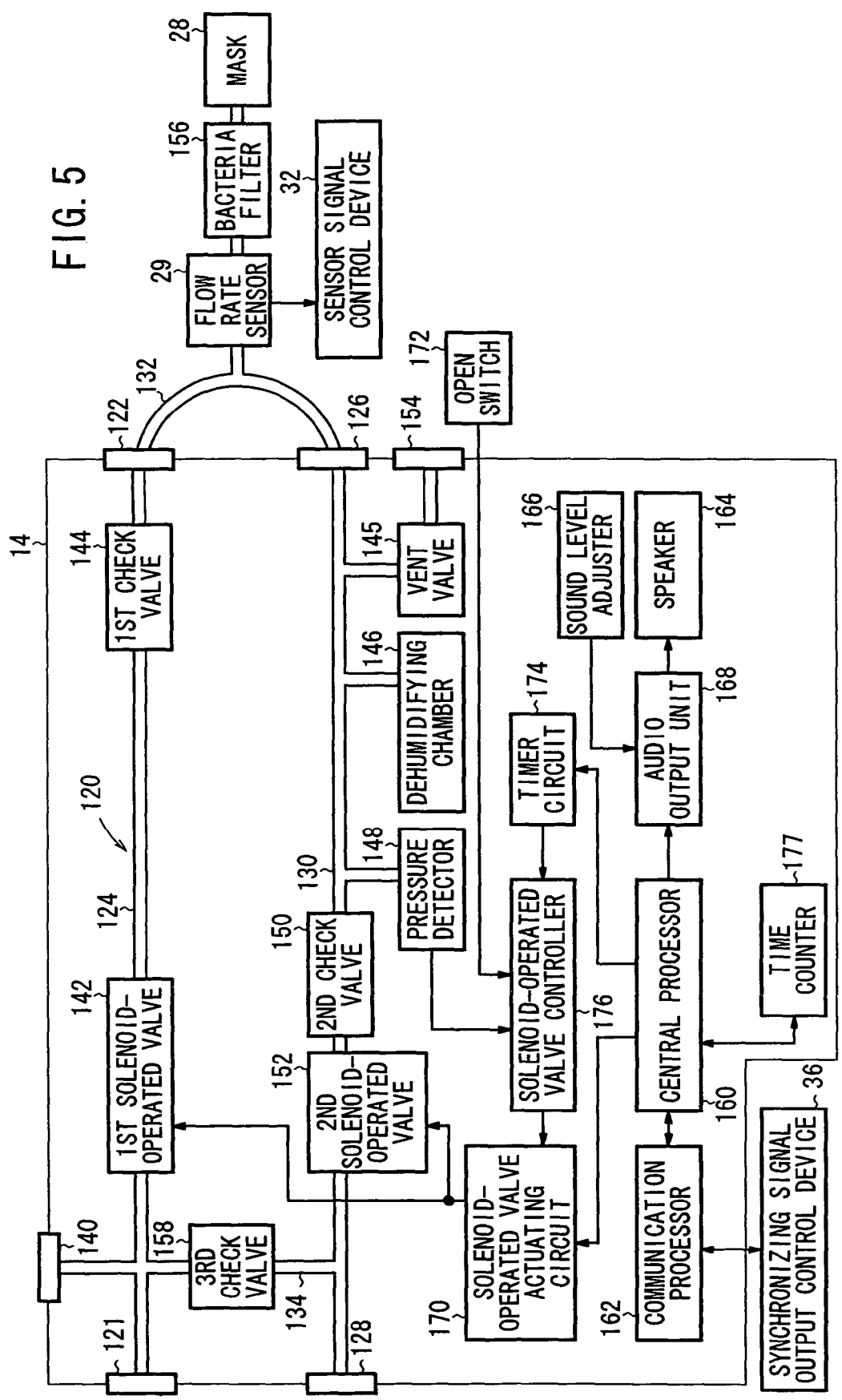
FIG. 5 is a block diagram of the respiration control apparatus according to the embodiment of the present invention.

The respiration control apparatus 14 has a respiration circuit 120 shown in FIG. 5. As shown in FIG. 5, the respiration circuit 120 basically comprises an inhalation circuit 124 (first circuit) having an inhalation inlet 121 and an inhalation outlet 122, an exhalation circuit 130 (second circuit) having an exhalation inlet 126 and an exhalation outlet 128, a first relay circuit 132 interconnecting the inhalation outlet 122 and the exhalation inlet 126, and a second relay circuit 134 interconnecting the inhalation circuit 124 near the inhalation inlet 121 and the exhalation circuit 130 near the exhalation outlet 128.

The inhalation circuit 124 includes, successively from the inhalation inlet 121, a junction port 140 connectable to an oxygen source for supplying oxygen to the respiration circuit 120, a first solenoid-operated valve 142 for selectively connecting and disconnecting the inhalation inlet 121 and the inhalation outlet 122, and a first check valve 144 for preventing exhaled air of the controlled body M from flowing into the inhalation circuit 124.

The exhalation circuit 130 includes, successively from the exhalation inlet 126, a vent valve 145 for connecting the exhalation circuit 130 to a forced outlet 154 when the pressure in the exhalation circuit 130 reaches a predetermined pressure, a dehumidifying chamber 146 housing a silica gel or the like for dehumidifying the interior of the exhalation circuit 130, a pressure detector 148 for detecting the pressure in the exhalation circuit 130 and outputting a signal representative of the detected pressure, a second check valve 150 for preventing air from being inhaled by the controlled body M through the exhalation circuit 130, and a second solenoid-operated valve 152 for selectively connecting and disconnecting the exhalation inlet 126 and the exhalation outlet 128.

Each of the first solenoid-operated valve 142 and the second solenoid-operated valve 152 comprises a solenoid-operated valve which is opened when its solenoid is de-energized.

To the first relay circuit 132, there are successively connected the flow rate sensor 29, a bacteria filter 156 for removing bacteria, and the mask 28 which is to be connected to the mouth of the controlled body M.

The second relay circuit 134 has a third check valve 158 for preventing a gas from flowing from the exhalation circuit 130 into the inhalation circuit 124. The second relay circuit 134 and the third check valve 158 are added in order to provide an air flow when a xenon gas inhaling device having a closed respiration circuit, for example, is connected between the inhalation inlet 121 and the exhalation outlet 128.

The respiration control apparatus 14 also has a central processor 160 (controller) for controlling the respiration circuit 120. To the central processor 160, there are connected a communication processor 162 for communicating with the synchronizing signal output control device 36, an audio output unit 168 connected to a speaker 164 for announcing audio information and a sound level adjuster 166, a solenoid-operated valve actuating circuit 170 for actuating the first solenoid-operated valve 142 and the second solenoid-operated valve 152, a timer circuit 174, and a time counter 177.

The respiration control apparatus 14 also has a solenoid-operated valve controller 176 which is supplied with output signals from an open switch 172 which can be operated by the controlled body M or the operator such as a doctor or the like in case of emergency, the pressure detector 148, and the timer circuit 174. The solenoid-operated valve controller 176 operates independently of the central processor 160 to directly control the solenoid-operated valve actuating circuit 170 based on the supplied output signals for thereby forcibly connecting the respiratory system of the controlled body M to the outside of the respiration control apparatus 14.

The radiation image capturing system 10 which incorporates the respiration control apparatus 14 according to the embodiment of the present invention is basically constructed as described above. Operation of the radiation image capturing system 10 will be described below with reference to FIG. 6.

With the controlled body M placed on the bed 17, a sensor for acquiring a respiration signal of the controlled body M is automatically selected in step S1. Specifically, the sensor selector 46 of the sensor signal control device 32 selects one of the sensors based on a preset priority order. For example, on the assumption that the priority order is preset according to the laser sensor 24, the flow rate sensor 29, and the load cell 26, with the priority order of the load cell 26 being lowest, if the load cell 26 is connected at all times to the sensor signal control device 32 and then the laser sensor 24 or the flow-rate sensor 29 is connected to the sensor signal control device 32, then the sensor selector 46 selects the laser sensor 24 or the flow rate sensor 29. The laser sensor 24 or the flow rate sensor 29 may automatically be selected without removing the load cell 26.

Next, the selected sensor is adjusted in step S2. For example, if the laser sensor 24 is selected, the distance between the laser sensor 24 and the controlled body M is adjusted, and then laser sensor 24 is fixed in position.

Thereafter, the respiration control apparatus 14 is installed in step S3. Specifically, the mask 28 is attached to the mouth of the controlled body M, and the communication processor 86 of the synchronizing signal output control device 36 and the communication processor 162 of the respiration control apparatus 14 are connected to each other by a cable or the like.

At this time, the first solenoid-operated valve 142 and the second solenoid-operated valve 152 of the respiration control apparatus 14 are open, connecting the controlled body M to the outside of the respiration control apparatus 14 through the respiration circuit 120. Therefore, the controlled body M can freely respire. Specifically, a gas introduced from the inhalation inlet 121 or the junction port 140 is supplied through the first solenoid-operated valve 142, the inhalation circuit 124, and the first check valve 144 as an inhalant gas to the controlled body M. Exhaled air from the controlled body M is discharged through the exhalation circuit 130, the second check valve 150, and the second solenoid-operated valve 152 from the exhalation outlet 128. The exhaled air from the controlled body M is dehumidified by the silica gel or the like housed in the dehumidifying chamber 146, thus preventing moisture condensation within the exhalation circuit 130.

If the sensor selector 46 has selected the flow rate sensor 29, then the respiratory state of the controlled body M is detected by the flow rate sensor 29, which supplies a respiration signal representative of the detected respiratory state to the sensor signal control device 32. The sensor signal control device 32 adjusts the amplitude and offset of the respiration signal, and standardize the respiration signal so as to make it independent of the type of the sensor, the individual properties of the controlled body M, and imaging conditions in step S4.

The synchronizing signal output control device 36 displays the waveform of the adjusted respiration signal on the CRT of the input/output device 112 in step S5. The operator sets respiration control conditions based on the displayed waveform of the respiration signal in step S6.

The respiration control conditions will be described in detail below with reference to FIG. 7. The respiration control conditions includes five conditions, i.e., (1) a respiration phase condition indicative of whether the respiration control is to be started in an inhalation phase or an exhalation phase, (2) a respiration level condition indicative of which respiration level (see level "a" in FIG. 7) the respiration control is to be started at, (3) a respiration control time condition indicative of how long a respiration control time (see a time T1 in FIG. 7) is to be, (4) a synchronizing signal output delay time condition indicative of a delay time (see a time T2 in FIG. 7) which is to elapse after the respiration control is started before a synchronizing signal is to be outputted, and (5) a respiration count condition indicative of the respiration phase (Dth respiration phase in FIG. 7) at which the respiration control is started after a control start time T0.

After desired respiration control conditions (1) through (5) have been set, the radiation image capturing system 10 starts capturing a radiation image in step S7. Specifically, the operator gives an instruction to capture a radiation image from the mouse or keyboard of the input/output device 112. At the control start time T0 shown in FIG. 7, the signal processor 80 of the synchronizing signal output control device 36 transfers a control start command Q1 as a respiration control signal through the communication processor 86 to the respiration control apparatus 14. The central processor 160 of the respiration control apparatus 14 receives the control start command Q1 through the communication processor 162, and controls the audio output unit 168 to produce an audio guidance such as "RESPIRATION CONTROL WILL BEGIN" from the speaker 164, indicating to the controlled body M that a respiration control cycle will be started.

The signal processor 80 of the synchronizing signal output control device 36 acquires the respiration signal indicative of the respiratory state of the controlled body M through the sensor signal control device 32 and the synchronizing signal output device 34 in step S8.

It is assumed that the respiration control cycle for the control time T1 (the respiration control time condition (3)) is to be started when the respiration level at the Dth inhalation phase (the respiration phase condition (1), the respiration count condition (5)) from the control start time T0 has reached the level "a" (the respiration level condition (2)), and a synchronizing signal is outputted after elapse of the time T2 (the synchronizing signal output delay time condition (4)) from the start of the respiration control cycle.

The signal processor 80 compares the acquired respiration signal with the respiration control conditions. (1), (2), (5) set in step S6, determines whether the respiration signal satisfies the respiration control conditions (1), (2), (5) or not in step S9. If the respiration signal does not satisfy the respiration control conditions (1), (2), (5), then the signal processor 80 repeats step S9 until the respiration signal satisfies the respiration control conditions (1), (2), (5).

If it is judged that the respiration signal satisfies the respiration control conditions (1), (2), (5), then the respiration control cycle is started in step S10. The signal processor 80 of the synchronizing signal output control device 36 transfers a respiration control time setting command Q2 and a respiration control start command Q3, which are respiration control signals, through the communication processor 86 to the respiration control apparatus 14.

Figure 7:
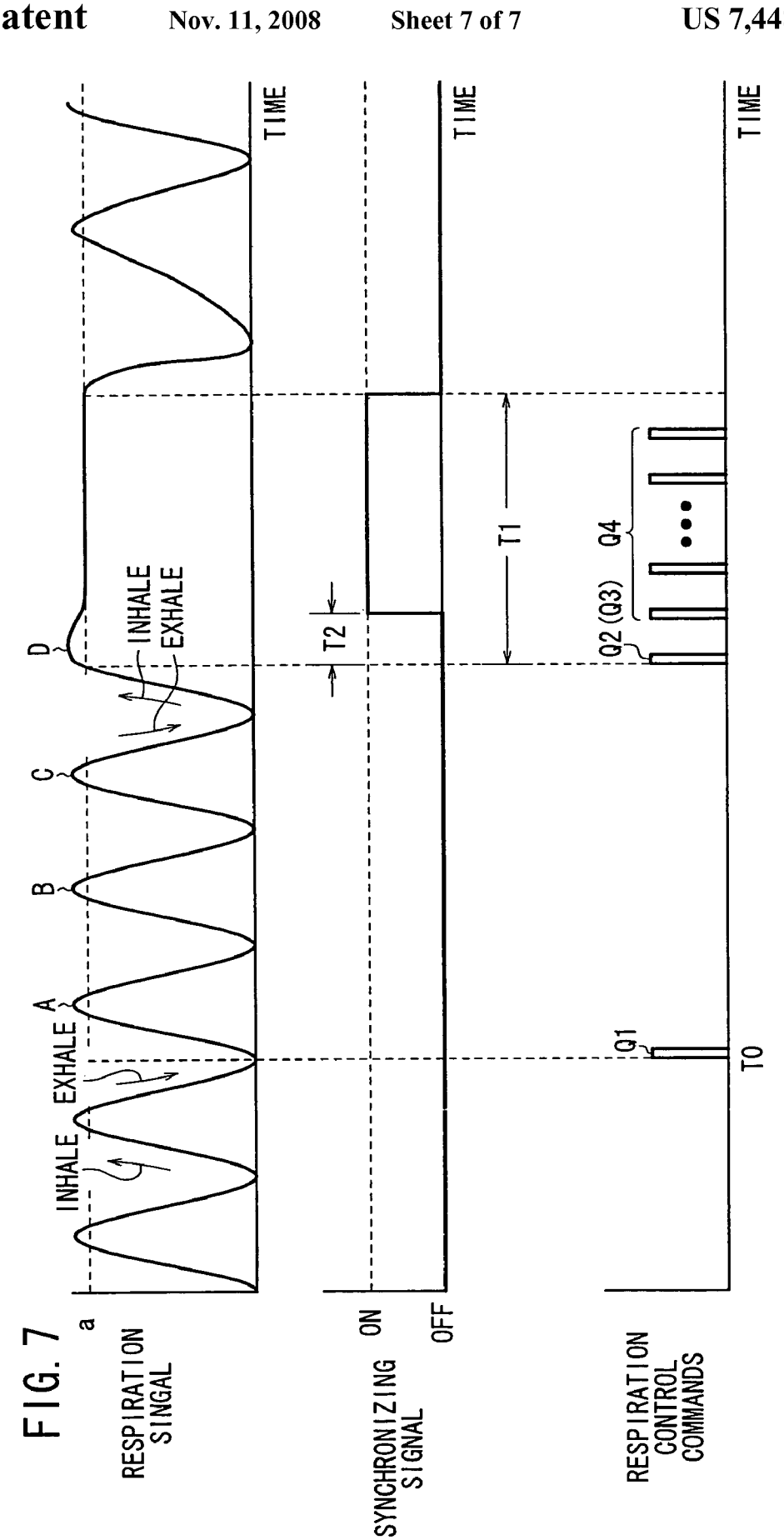
FIG. 7 is a diagram showing respiration control conditions that are established for the synchronizing signal output control device.

In response to the respiration control time setting command Q2, the central processor 160 of the respiration control apparatus 14 sets a time setting in the respiration control time setting command Q2, i.e., the time T1 shown in FIG. 7, in a register of the time counter 177, which starts measuring time. The central processor 160 also sets a limit processing time T3 (T3>T1) for the respiration control cycle in a register of the timer circuit 174, which starts measuring time. The limit processing time T3 is, for example, of an optimum value in an allowable limit range for the controlled body M.

In response to the respiration control start command Q3, the central processor 160 controls the solenoid-operated valve actuating circuit 170 to close the first solenoid-operated valve 142 and the second solenoid-operated valve 152. When the first solenoid-operated valve 142 and the second solenoid-operated valve 152 are closed, the inhalation circuit 124 and the exhalation circuit 130 are closed, disconnecting the respiratory system of the controlled body M from the outside of the respiration control apparatus 14.

After elapse of the time T2 (see FIG. 7) satisfying the synchronizing signal output delay time condition (4) after it has been judged that the respiration signal satisfies the respiration control conditions (1), (2), (5), the signal processor 80 outputs a synchronizing signal in step S11.

The synchronizing signal generated by the signal processor 80 is supplied through the synchronizing signal output unit 82 to the synchronizing signal output device 34, and thereafter supplied from the synchronizing signal output unit 62 to the X-ray control device 15. When supplied with the synchronizing signal, the X-ray control device 15 outputs a shot signal to the high-voltage generating device 16. In response to the supplied shot, the high-voltage generating device 16 applies a high voltage to energize the k-ray source 18 to apply X rays to the controlled body M in step S12.

The X-ray detector 19, which is located across the controlled body M from the X-ray source 18, detects X-rays that have passed through the controlled body M and receives transmitted data. The transmitted data is collected by the data collecting device 20, and then transferred to the image reconstructing device 21, which reconstructs a tomographic image of the controlled body M from the transmitted data. The reconstructed tomographic image is displayed by the image display device 22 for diagnosis.

While the X-rays are being applied to the controlled body M, the respiration control apparatus 14 controls the controlled body M to stop its respiration. Therefore, the movement of a respiratory moving object, such as an organ in the controlled body M, is prevented. A clear reconstructed tomographic image free of artifacts is obtained.

During the respiration control period (the time T1 in FIG. 7), the signal processor 80 transfers a respiration control remaining time command Q4, which is a respiration signal, to the respiration control apparatus 14. The respiration control remaining time command Q4 represents a remaining time of the respiration control cycle, and comprises data indicative of, for example, "remaining time=15 seconds", "remaining time=10 seconds". The signal processor 80 may produce a plurality of respiration control remaining time commands Q4 at intervals of 5 seconds, for example, or a single respiration control remaining time command Q4, within the respiration control period.

In response to the respiration control remaining time command Q4, the central processor 160 of the respiration control apparatus 14 controls the audio output unit 168 to produce an audio guidance "REMAINING TIME OF RESPIRATION CONTROL CYCLE IS 15 SECONDS", for example, from the speaker 164, reporting the progress of the respiration control cycle successively to the controlled body M.

If the operator or the controlled body M instructs the input/output device 112 to interrupt the respiration control during the respiration control cycle, then the signal processor 80 transfers a respiration control cycle interrupt command through the communication processor 86 to the respiration control apparatus 14. The central processor 160 then performs a processing sequence based on the respiration control cycle interrupt command given the highest priority. Specifically, the central processor 160 controls the solenoid-operated valve actuating circuit 170 to open the first solenoid-operated valve 142 and the second solenoid-operated valve 152, quickly allowing the controlled body M to respire on its own.

Thereafter, the signal processor 80 determines whether the respiration control time T1 has elapsed or not in step S13. If the respiration control time T1 has elapsed, then the signal processor 80 stops outputting the synchronizing signal in step S14.

The central processor 160 of the respiration control apparatus 14 monitors a time counting end signal from the time counter 177. When the central processor 160 receives the time counting end signal, the central processor 160 controls the solenoid-operated valve actuating circuit 170 to open the first solenoid-operated valve 142 and the second solenoid-operated valve 152. When the first solenoid-operated valve 142 and the second solenoid-operated valve 152 are opened, the respiration circuit 120 is opened, canceling the stoppage of the respiration of the controlled body M and allowing the controlled body M to respire on its own.

The central processor 160 controls the audio output unit 168 to produce an audio guidance "RESPIRATION CONTROL CYCLE IS FINISHED", for example, from the speaker 164, reporting to the controlled body M that the respiration control cycle is finished.

Figure 6:
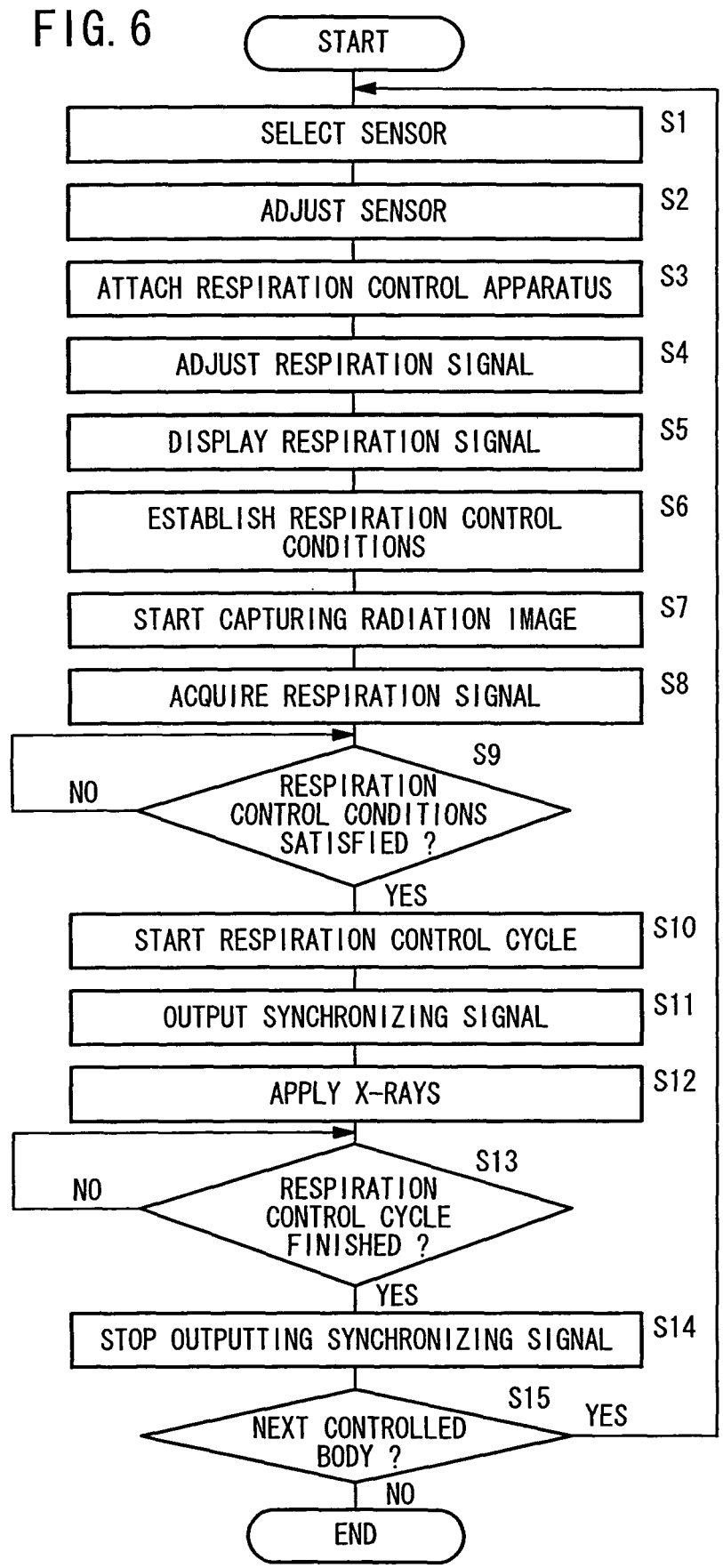
FIG. 6 is a flowchart of an operation sequence of the radiation image capturing system.

After the image reconstructing device 21 has reconstructed the tomographic image of the controlled body M from the transmitted data based on the X-rays, the synchronizing signal generating apparatus 12 confirms whether there is a next controlled body M or not in step S15. If there is a next controlled body M to be imaged, then the operation sequence from step S1 shown in FIG. 6 is repeated. If there is none, then the operation sequence of the radiation image capturing system 10 is finished.

Upon elapse of the limit processing time T3 from the start of the respiration control cycle, the timer circuit 174 ends its time measuring cycle and outputs a time measuring cycle end signal to the solenoid-operated valve controller 176, independently of the process for controlling the first solenoid-operated valve 142 and the second solenoid-operated valve 152 with the central processor 160. In response to the time measuring cycle end signal, the solenoid-operated valve controller 176 controls the solenoid-operated valve actuating circuit 170 to open the first solenoid-operated valve 142 and the second solenoid-operated valve 152. When the first solenoid-operated valve 142 and the second solenoid-operated valve 152 are opened, the respiration circuit 120 is opened, allowing the controlled body M to respire on its own. Consequently, even when the central processor 160 does not output a control signal to the solenoid-operated valve actuating circuit 170 to actuate first solenoid-operated valve 142 and the second solenoid-operated valve 152, the time measuring cycle end signal supplied from the timer circuit 174 enables the solenoid-operated valve controller 176 to control the solenoid-operated valve actuating circuit 170 to open the first solenoid-operated valve 142 and the second solenoid-operated valve 152.

If the pressure detector 148 detects when the pressure in the exhalation circuit 130 exceeds a predetermined pressure level, then the pressure detector 148 outputs a detected pressure signal to the solenoid-operated valve controller 176. Based on the detected pressure signal, the solenoid-operated valve controller 176 controls the solenoid-operated valve actuating circuit 170 to open the first solenoid-operated valve 142 and the second solenoid-operated valve 152. When the first solenoid-operated valve 142 and the second solenoid-operated valve 152 are opened, the respiration circuit 120 is opened, allowing the controlled body M to respire on its own.

If the operator or the controlled body M operates the open switch 172, then the open switch 172 applies an open signal to the solenoid-operated valve controller 176. Based on the open signal, the solenoid-operated valve controller 176 controls the solenoid-operated valve actuating circuit. 170 to open the first solenoid-operated valve 142 and the second solenoid-operated valve 152. When the first solenoid-operated valve 142 and the second solenoid-operated valve 152 are opened, the respiration circuit 120 is opened, allowing the controlled body M to respire on its own.

If the pressure in the exhalation circuit 130 reaches a predetermined pressure level set for the vent valve 145, then the vent valve 145 is opened, connecting the exhalation circuit 130 to the forced outlet 154. When the exhalation circuit 130 is thus connected to the forced outlet 154, the controlled body M can thus breathe in the presence of the predetermined pressure in the exhalation circuit 130.

Since each of the first solenoid-operated valve 142 and the second solenoid-operated valve 152 comprises a solenoid-operated valve which is opened when its solenoid is de-energized, even when a power failure occurs, for example, while the respiration control apparatus 14 is in operation, the respiration circuit 120 is opened, allowing the controlled body M to respire on its own.

Although a certain preferred embodiment of the present invention has been shown and described in detail, it should be understood that various changes and modifications may be made therein without departing from the scope of the appended claims.

What is claimed is:

1. An apparatus having at least five respective valves disposed therein for controlling respiration of a controlled body, comprising:
    a first circuit having an end adapted to be connected to said controlled body and an opposite end connected to the outside of the apparatus;
    two respective valves disposed independently in said first circuit, said respective valves comprising:
        a first check valve disposed in said first circuit for allowing said controlled body to inhale from said outside through said first circuit and preventing exhaled air from said controlled body from flowing into said first circuit; and
        a first solenoid-operated valve disposed in said first circuit for selectively connecting and disconnecting a respiratory system of said controlled body to and from said outside;
    a second circuit having an end adapted to be connected to said controlled body and an opposite end connected to said outside;
    three other respective valves disposed independently in said second circuit, said other respective valves comprising:
        a second check valve disposed in said second circuit for allowing said controlled body to exhale to the outside through said second circuit and preventing said controlled body from inhaling through said second circuit;
        a second solenoid-operated valve disposed in said second circuit for selectively connecting and disconnecting the respiratory system of said controlled body to and from said outside; and
        a third check valve for preventing flow from the second circuit to the first circuit; and
    control means for controlling said first solenoid-operated valve and said second solenoid-operated valve at a predetermined time in a respiratory cycle thereby to disconnect the respiratory system of said controlled body from said outside, and for controlling said first solenoid-operated valve and said second solenoid-operated valve after elapse of a predetermined period from said predetermined time thereby to connect the respiratory system of said controlled body to said outside.

2. An apparatus according to claim 1, further comprising:
    a timer circuit for starting to measure time when said first solenoid-operated valve and said second solenoid-operated valve have started to disconnect the respiratory system of said controlled body from said outside, and outputting a time measuring cycle end signal after elapse of a predetermined period from starting to measure time; and
    a solenoid-operated valve controller responsive to said time measuring cycle end signal, for controlling said first solenoid-operated valve and said second solenoid-operated valve, independently of said control means, to connect the respiratory system of said controlled body to said outside.

3. An apparatus according to claim 1, further comprising:
    a pressure detector for detecting when an exhaling pressure in said second circuit reaches a predetermined pressure and outputting a detected pressure signal; and
    a solenoid-operated valve controller responsive to said detected pressure signal, for controlling said first solenoid-operated valve and said second solenoid-operated valve, independently of said control means, to connect the respiratory system of said controlled body to said outside.

4. An apparatus according to claim 1, further comprising:
    an open switch for outputting an open signal when operated; and
    a solenoid-operated valve controller responsive to said open signal, for controlling said first solenoid-operated valve and said second solenoid-operated valve, independently of said control mean, to connect the respiratory system of said controlled body to said outside.

5. An apparatus according to claim 1, further comprising:
    a vent valve disposed in said second circuit, for connecting said second circuit to said outside in the presence of a predetermined exhaling pressure or higher in said second circuit.

6. An apparatus according to claim 1, wherein said first solenoid-operated valve and said second solenoid-operated valve connect the respiratory system of said controlled body to said outside when said first solenoid-operated valve and said second solenoid-operated valve are de-energized.

7. An apparatus according to claim 1, further comprising:
    an audio output unit for announcing the progress of a respiration control cycle of said control means by voice.

8. An apparatus according to claim 1, further comprising:

a flow rate sensor for detecting a respiratory state of said controlled body as an air flow rate, said flow rate sensor being connected between said first circuit and said second circuit and said controlled body;

said control means comprising means for controlling said first solenoid-operated valve and said second solenoid-operated valve based on said detected air flow rate.

9. An apparatus according to claim 1, further comprising:
a filter for removing bacteria, said filter being connected between said first circuit and said controlled body.

10. An apparatus according to claim 1, wherein said second circuit includes a dehumidifying chamber for dehumidifying exhaled air from said controlled body.

11. An apparatus according to claim 10, wherein said dehumidifying chamber houses a silica gel therein.

* * * * *